US007939295B2

(12) United States Patent
Carr et al.

(10) Patent No.: US 7,939,295 B2
(45) Date of Patent: May 10, 2011

(54) METHODS FOR REDUCING IMMUNOGENICITY OF POLYPEPTIDES

(75) Inventors: Francis J. Carr, Balmedie (GB); Graham Carter, By Newmachar (GB); Koen Hellendoorn, Newmarket (GB)

(73) Assignee: Merck Patent GmbH, Darmstadt (DE)

( * ) Notice: Subject to any disclaimer, the term of this patent is extended or adjusted under 35 U.S.C. 154(b) by 1987 days.

(21) Appl. No.: 10/483,153

(22) PCT Filed: Jul. 12, 2002

(86) PCT No.: PCT/EP02/07785
§ 371 (c)(1),
(2), (4) Date: Jan. 8, 2004

(87) PCT Pub. No.: WO03/006047
PCT Pub. Date: Jan. 23, 2003

(65) Prior Publication Data
US 2004/0185038 A1    Sep. 23, 2004

(30) Foreign Application Priority Data

Jul. 13, 2001  (EP) .................................... 01117105
Jul. 17, 2001  (EP) .................................... 01117267
Jul. 17, 2001  (EP) .................................... 01117271

(51) Int. Cl.
*C12N 15/09* (2006.01)
(52) U.S. Cl. ...................................... 435/69.3; 435/69.7
(58) Field of Classification Search ........................ None
See application file for complete search history.

(56) References Cited

U.S. PATENT DOCUMENTS
6,936,249 B1 * 8/2005 Estell et al. ................ 424/184.1

OTHER PUBLICATIONS

Weiss, A. in Fundamental Immunology 2nd Edition [1989], editor W. Paul. Raven Press, New York. pp. 359-384.*
Rider et al., Molecular Immunology vol. 33, No. I/8, pp. 625-633.*
Viret et al., Immunity, vol. 10, 559-568, May 1999.*
Kropshofer et al., J. Exp. Med., vol. 175 Jun. 1992, 1799-1803.*
Goldsby et al., Immunology, 5th ed., W.H. Freeman and Co., pp. 171-177 and 193-196.*
Kropshofer et al., Proc. Natl. Acad. Sci. USA, vol. 90, pp. 403-407, Jan. 1993.*

* cited by examiner

*Primary Examiner* — Zachary Skelding
(74) *Attorney, Agent, or Firm* — Olson & Cepuritis, Ltd.

(57) ABSTRACT

This invention relates to the fields of immunology and protein therapeutics. The therapeutic proteins are polypeptides to be administered especially to humans. The polypeptides are modified whereby the modification results in a reduced propensity for the polypeptide to elicit an immune response upon administration to the human subject. The invention therefor provides methods for the development of therapeutic polypeptides that are less immunogenic than any non-modified counterpart when used in vivo. The modifications used according to this invention relate, for example, to the introduction of protease cleavage sites, attachment of different molecules or insertion of non-natural amino acids.

3 Claims, No Drawings

SEQUENCE LISTING

<160> NUMBER OF SEQ ID NOS: 1

<210> SEQ ID NO 1
<211> LENGTH: 16

-continued

```
<212> TYPE: PRT
<213> ORGANISM: Homo sapiens
<220> FEATURE:

<400> SEQUENCE: 1

Ala Ile Leu Glu Phe Arg Ala Met Ala Gln Phe Ser Arg Lys Thr Asp
 1               5                  10                  15
```

METHODS FOR REDUCING IMMUNOGENICITY OF POLYPEPTIDES

This application is the National Stage of International Application No. PCT/EP02/07785, filed on Jul. 12, 2002.

FIELD OF THE INVENTION

The invention relates to the fields of immunology and protein therapeutics. The therapeutic proteins are polypeptides to be administered especially to humans. The polypeptides are modified whereby the modification results in a reduced propensity for the polypeptide to elicit an immune response upon administration to the human subject. The invention therefore provides methods for the development of therapeutic polypeptides that are less immunogenic than any non-modified counterpart when used in vivo.

BACKGROUND OF THE INVENTION

There are many instances whereby the efficacy of a therapeutic protein is limited by an unwanted immune reaction to the therapeutic protein. Several mouse monoclonal antibodies have shown promise as therapies in a number of human disease settings but in certain cases have failed due to the induction of significant degrees of a human anti-murine antibody (HAMA) response [Schroff, R. W. et al (1985) *Cancer Res.* 45: 879-885; Shawler, D. L. et al (1985) *J. Immunol.* 135: 1530-1535]. For monoclonal antibodies, a number of techniques have been developed in attempt to reduce the HAMA response [WO 89/09622; EP 0239400; EP 0438310; WO 91/06667]. These recombinant DNA approaches have generally reduced the mouse genetic information in the final antibody construct whilst increasing the human genetic information in the final construct. Notwithstanding, the resultant "humanised" antibodies have, in several cases, still elicited an immune response in patients [Issacs J. D. (1990) *Sem. Immunol.* 2: 449, 456; Rebello, P. R. et al (1999) *Transplantation* 68: 1417-1420].

Antibodies are not the only class of polypeptide molecule administered as a therapeutic agent against which an immune response may be mounted. Even proteins of human origin and with the same amino acid sequences as occur within humans can still induce an immune response in humans. Notable examples include the therapeutic use of granulocyte-macrophage colony stimulating factor [Wadhwa, M. et al (1999) *Clin. Cancer Res.* 5: 1353-1361] and interferon alpha 2 [Russo, D. et al (1996) *Bri. J. Haem.* 94: 300-305; Stein, R. et al (1988) *New Engl. J. Med.* 318: 1409-1413] amongst others.

An immune response to a therapeutic protein proceeds via the MHC class II peptide presentation pathway. Here exogenous proteins are engulfed and processed for presentation in association with MHC class II molecules of the DR, DQ or DP type. MHC Class II molecules are expressed by professional antigen presenting cells (APCs), such as macrophages and dendritic cells amongst others. Engagement of a MHC class II peptide complex by a cognate T-cell receptor on the surface of the T-cell, together with the cross-binding of certain other co-receptors such as the CD4 molecule, can induce an activated state within the T-cell. Activation leads to the release of cytokines further activating other lymphocytes such as B cells to produce antibodies or activating T killer cells as a full cellular immune response.

A principal factor in the induction of an immune response therefore is the presence within the protein of peptides that can stimulate the activity of T-cells via presentation on MHC class II molecules, so-called "T-cell epitopes". Such potential T-cell epitopes are commonly defined as any amino acid residue sequence with the ability to bind to MHC Class II molecules. Such T-cell epitopes can be measured to establish MHC binding. Implicitly, a "T-cell epitope" means an epitope which when bound to MHC molecules can be recognized by a T-cell receptor (TCR), and which can, at least in principle, cause the activation of these T-cells by engaging a TCR to promote a T-cell response. It is, however, usually understood that certain peptides which are found to bind to MHC Class II molecules may be retained in a protein sequence because such peptides are recognised as "self" within the organism into which the final protein is administered.

From the forgoing, it is clear that immunogenicity of a therapeutic protein strongly depends on the ability of the immune system to select and proliferate T-cell clones that are specific for peptides derived from the therapeutic protein. The activation of a specific T-cell clone is a complex event but one that occurs at the end of a pathway of complex events. The pathway can be characterised by several key steps;

1) protein uptake by antigen presenting cells;
2) proteolytic processing of the protein by proteases in the antigen presenting cells;
3) binding of peptides excised from the protein to the MHC molecules that are able to present these on the cell surface;
4) transport of peptides MHC complexes to the cell surface.

The present invention is concerned with solutions to the problem posed by the inevitable presence of immunogenic MHC class II epitopes within therapeutic proteins. In general aspect, the invention is concerned with disrupting the ability of peptide sequences to emerge from the above outlined pathway, and in particular provides methods by which steps 2-4, as outlined above, may be manipulated in the development of a therapeutic protein with an improved immunogenic profile.

In the art there are procedures for identifying synthetic peptides able to bind MHC class II molecules. Such peptides may not function as T-cell epitopes in all situations, particularly, in vivo due to the processing pathways or other phenomena. T-cell epitope identification may be considered as the first step to epitope elimination and computational techniques such as scanning for recognised sequence motifs in experimentally determined T-cell epitopes or by using computational techniques to predict MHC class II-binding peptides have been published. WO98/52976 and WO00/34317 teach computational threading approaches to identifying polypeptide sequences with the potential to bind a sub-set of human MHC class II DR allotypes. In these teachings, predicted T-cell epitopes are removed by the use of judicious amino acid substitution within the primary sequence of the therapeutic antibody or non-antibody protein of both non-human and human derivation. These procedures provide modified polypeptide sequences by amino acid substitution and do not anticipate the use of other modifying modalities in order to eliminate the epitope.

Other techniques exploiting soluble complexes of recombinant MHC molecules in combination with synthetic peptides and able to bind to T-cell clones from peripheral blood samples from human or experimental animal subjects have been used in the art [Kern, F. et al (1998) *Nature Medicine* 4:975-978; Kwok, W. W. et al (2001) *TRENDS in Immunol.* 22:583-588] and may equally be exploited in an epitope identification strategy, but also do not provide means for epitope elimination.

U.S. Pat. No. 5,833,991 (Masucci) provides a method for preventing undesired immune responses to recombinant proteins exploiting tracts of glycine-containing sequence, this approach is similar to widely practiced methods whereby an immunologically inhert species is adducted to a therapeutic protein for example a polymeric molecule such as PEG and has been intensively described in the art [for example schemes see U.S. Pat. No. 5,349,001 and WO90/13590].

For clarity in conveying understanding to the present invention, the major components of what we herein term the "immune processing pathway" are now described.

MHC Class II System

MHC Class II molecules are a group of highly polymorphic proteins which play a central role in helper T-cell selection and activation. The human leukocyte antigen group DR (HLA-DR) are the predominant isotype of this group of proteins, however, isotypes HLA-DQ and HLA-DP perform similar functions and are biologically relevant. The MHC class II DR molecule is made of an alpha and a beta chain that insert at their C-termini through the cell membrane. Each hetero-dimer possesses a ligand binding domain which binds to peptides varying between 9 and 20 amino acids in length, although the binding groove can accommodate a maximum of 11 amino acids. The ligand binding domain is comprised of amino acids 1 to 85 of the alpha chain, and amino acids 1 to 94 of the beta chain. DQ molecules have recently been shown to have an homologous structure and the DP family proteins are also expected to be very similar. In humans approximately 70 different allotypes of the DR isotype are known, for DQ there are 30 different allotypes and for DP 47 different allotypes are known. Each individual bears two to four DR alleles, two DQ and two DP alleles. The structure of a number of DR molecules has been solved and such structures point to an open-ended peptide binding groove with a number of hydrophobic pockets which engage hydrophobic residues (pocket residues) of the peptide [Brown et al Nature (1993) 364: 33; Stern et al (1994) Nature 368: 215]. Polymorphism identifying the different allotypes of class II molecule contributes to a wide diversity of different binding surfaces for peptides within the peptide binding grove and at the population level ensures maximal flexibility with regard to the ability to recognize foreign proteins and mount an immune response to pathogenic organisms.

Proteolytic Processing

Protein antigens can be taken up by various mammalian cells for processing and APCs expressing MHC class II molecules are able to do this with particular efficiency. Antigens can enter the endocytic route by various mechanisms, such as receptor-mediated endocytosis, phagocytosis, macropinocytosis and autophagy. The antigen is degraded in endocytic vesicles, which are acidic and proteolyticaly active. Multiple different proteases participate in this pathway and many of which have not yet been characterised. Endocytic vesicles gradually change in character, becoming more acidic and more proteolyticaly active. The antigen is degraded in steps and the most sensitive or exposed areas will be attacked first.

Many different proteases have been identified in the endocytic vesicles of antigen presenting cells. Since most of these proteins are also found in other proteolytic processes in mammals, some are well characterised. In B cells and dendritic cells cathepsin S plays a key role, in thymus endothelial cells this is cathepsin L and in macrophages cathepsin F.

Cathepsins are papain family cysteine proteases involved in a variety of physiologic processes in addition to antigen presentation. Cathepsins are glycoproteins and contain an essential cysteine residue in their active site but differ in some enzymatic properties, including substrate specificities and pH stability. Some cathepsins have been identified have ubiquitous expression and may have 'housekeeping' roles, whereas others, like cathepsin S, have tissue-restricted expression and may have more specific functions.

In addition to cathepsins S, L and F, several other cathepsins involved in antigen degradation have been identified. These are cathepsin B, cathepsin H, cathepsin D and cathepsin E and potentially cathepsins Z, V and K. Since the pH-optimum for the various cathepsins differs, some are likely to be more active in early endosomes, while others play a role in the later stages of antigen processing. As a consequence the population of protein fragments will vary through the processing pathway, while there may also be a different range of peptides in different individual APCs. In addition to the cathepsins, other proteases such as asparagine endopeptidase, which plays a crucial role in the processing of antigens taken up by B-cells, may also be involved in the degradation of antigens.

Formation of the MHC Peptide Complex

Following the antigen degradation pathway, peptides will emerge that have the potential to bind in the binding groove of HLA-DR, HLA-DQ or HLA-DP molecules. In order for a peptide to bind to HLA-DR, HLA-DQ or HLA-DP molecules, it has to remove a peptide called CLIP (class II associated Ii peptide) from the binding groove. CLIP is a peptide derived from the Ii protein, which is a chaperone molecule, targeting HLA-DR, DQ and DP from the endoplasmic reticulum to the endocytic vesicles. Since Ii contains a (C-terminal) trimerization domain, nonameric complexes are formed. The cytoplasmic domain of Ii contains signal sequences, which target the complexes through the Golgi into the endocytic route. Here the Ii molecules are degraded in several stages. First the trimerization domain is cleaved off by a non-cysteine protease, so the nonamer dissociates leaving DRα-DRβ-IiP22 complexes. A Cys-protease cleaves C-terminally of the CLIP-region, thereby removing two bulky carbohydrates, leaving DRα-DRβ-IiP10. Finally Ii is cleaved at the N-terminus of the CLIP peptide, leaving DRα-DRβ-CLIP. The CLIP peptide can be exchanged for other peptides that are present in the endosomes.

In the exchange reaction of peptides binding to HLA-DR a molecule named HLA-DM, a MHC class Ii encoded enzyme, plays a key role by catalysing the exchange of CLIP peptides and other peptides that are bound to DRα-DRβ with a low affinity, for more stably binding peptides derived from processed antigens [reviewed by Busch et al., (2000), Curr. Op. Immunol. 12, 99-106]. HLA-DM has a great effect on the kinetics of the exchange reaction of peptides to purified HLA-DR in vitro, efficiently stimulating the release of certain peptides. The stoichiometry of HLA-DM and HLA-DR in endosomes is 1:5-1:12, while the turnover of DM in vitro is ca. 3-12/min. HLA-DM interacts with HLA-DR molecules via exposed hydrophobic regions and charged residues. The most likely sites of interaction have been proposed on a crystal structure model of HLA-DM [Mosyak et al., (1998) Immunity 9:377-383]. HLA-DM preferentially binds to HLA-DR complexes to which a peptide has bound with low affinity. Besides this, it can also bind to empty HLA-DR dimers, which are unstable and likely to aggregate in the absence of HLA-DM. The binding of HLA-DM stabilises the 'empty state' of the HLA-DR dimers to which peptide is bound loosely or no peptide is bound at all. By keeping the binding groove of HLA-DR open in this way, peptides can compete for binding in this groove. The exchange of peptides can also take place in the absence of HLA-DM in vivo, albeit with a significantly reduced efficiency. The N-terminal domain of the CLIP peptide can interact with some HLA-DR allotypes outside the binding groove and thereby stabilise a conformation in which the CLIP peptide is more likely to be released. HLA-DM action is also no absolute requirement for the transport of HLA-DR complexes to the plasma membrane. In the absence of HLA-DM, class II molecules with CLIP peptides of self-peptides still bound can make their way to the cell surface.

HLA-DM has maximal activity at acidic pH and will therefore be mainly active in the proteolytic endosomes (called MIIC). In the acidic MIICs HLA-DM will be discharged after a peptide has stably bound in the antigen binding groove of HLA-DR. Alternatively HLA-DM can be co-transported with the HLA-DR complex to the cell surface, where the neutral pH leads to a quick release. Indeed, small amounts of HLA-DM can be found at the cell surface, where they may have a functional role [Arndt et al. (2000), *EMBO J.* 19:6, 1241-1251]. Subsequently HLA-DM, which contains a lysosomal targeting signal, is quickly internalised and retargeted to the MIICs.

An MHC class II encoded protein named HLA-DO has a regulatory function [reviewed by van Ham et al., (2000), *Immunogen.* 51, 765-770], inhibiting HLA-DM activity in a pH dependent manner [van Ham et al. (1997), *Curr. Biol.* 7, 950-957]. HLA-DM has optimal activity at pH 5, but is also active at pH 6. Binding of HLA-DO at pH6 abolishes HLA-DM activity. Thus, HLA-DO acts as a pH sensor for HLA-DM activity, inhibiting it in early endosomes but allowing activity at lysosomal pH. Indeed in HLA-DO minus cells, HLA-DR can be found loaded with long peptides that have not yet been fully processed, while in HLA-DO positive cells binding of those peptides to HLA-DR does not take place.

While HLA-DM is expressed in all APCs, HLA-DO is mainly found in B-cells. It has been suggested that this is a way to specifically stimulate the presentation of epitopes derived from antigens that were internalised through B-cell receptor mediated uptake. When antibody-bound antigens are endocytosed by B-cells, they are quickly transported to MIIC, the late-stage protein processing vesicles. Since HLA-DO is not functioning in these compartments because of the acidic pH, peptides that are excised from these antigens will quickly bind to HLA-DR. Peptides produced in early endosomes, i.e. endosomes where HLA-DO suppresses HLA-DM function due to the pH, from antigens taken up by non-receptor mediated endocytosis, will be prevented from binding to HLA-DR [van Ham et al. (2000), *J. Exp. Med* 191:7, 1127-1136].

The binding groove of HLA-DR, DQ and DP dimers contain several pockets in which amino acids of the antigenic peptide may bind. The so-called anchor residues of peptides, which may bind in these pockets, are the main determinants for binding of peptides to HLA-DR, DQ and DP. Binding to the MHC is a competitive process and peptides with high affinity are known to compete successfully for lower affinity peptides favouring their presentation on the surface of the APC [Adorni L. et al (1988) *J. Exp. Med* 168:2091; Ii. W. et al (1992) *Eur. J. Immunol.* 22: 943]. For some peptides the affinity is so high as to constitute effectively an irreversible binding reaction [Lanzavecchia A. et al (1992) *Nature* 357: 249].

SUMMARY OF THE INVENTION

As depicted above and as consequence thereof, it would be desirable to identify and to remove or at least to reduce the effectiveness of any given T-cell epitope from any therapeutically valuable but originally immunogenic peptide, polypeptide or protein. It is an objective of the present invention to provide modes by which the inevitable presence of a T-cell epitope need not lead to an immunogenic response to the protein upon its administration as a therapeutic molecule. Accordingly there are provided herein multiple methodological options within the theme of providing for the elimination or amelioration of the immunogenic potential of a therapeutic protein.

In summary the invention relates to the following issues:

a modified polypeptide in which the modification disrupts the ability of the peptide to act as an MHC class II ligand;

modified polypeptides with reduced capacity for presentation to the immune system by the MHC class II pathway;

a modified polypeptide being substantially non-immunogenic or less immunogenic than any non-modified polypeptide having the same biological activity when used in vivo;

an accordingly modified polypeptide wherein the modification is the substitution of specific amino acid residues within a polypeptide chain for a respective D-isomeric form;

an accordingly modified polypeptide wherein the modification is a covalent attachment of a chemical group;

an accordingly modified polypeptide wherein the modification introduces a signal sequence capable of directing post-translational modification of the polypeptide in a suitable host and wherein the post-translational modification renders the polypeptide unable to be presented in conjunction with an MHC class II molecule;

an accordingly modified polypeptide wherein the modification introduces a signal sequence capable of directing post-translational modification of the polypeptide in a suitable host and wherein the post-translational modification renders the polypeptide unable to be presented in conjunction with an MHC class II molecule;

an accordingly specified polypeptide, wherein said loss of immunogenicity is achieved by amino acid substitution, addition or deletion, wherein the alteration of the amino acid sequence is conducted at a position which in the non-modified polypeptide is liable to cleavage by a protease of the MHC class II proteolytic pathway;

an accordingly specified polypeptide, wherein said loss of immunogenicity is achieved by amino acid substitution, addition or deletion, wherein the alteration of the amino acid sequence is conducted at a position which in the non-modified polypeptide remains uncleaved by a protease of the MHC class II proteolytic pathway;

an accordingly specified polypeptide, wherein said loss of immunogenicity is achieved by amino acid substitution, addition or deletion, wherein the alteration of the amino acid sequence is conducted to result in the introduction of a new cleavage site for a protease of the MHC class II proteolytic pathway;

an accordingly specified polypeptide, wherein said loss of immunogenicity is achieved by amino acid substitution, addition or deletion, wherein the alteration of the amino acid sequence is conducted at a position which in the non-modified polypeptide is a T-cell epitope and the alteration renders the T-cell epitope unable to survive the processing pathway for MHC class II presentation for reason of peptide cleavage;

an accordingly specified polypeptide, wherein said loss of immunogenicity is achieved by amino acid substitution, addition or deletion, wherein the alteration of the amino acid sequence is conducted at a position which in the non-modified polypeptide is a T-cell epitope and the alteration renders the T-cell epitope unable to survive the processing pathway for MHC class II presentation for reason of loss of interaction with Ii;

an accordingly specified polypeptide, wherein said loss of immunogenicity is achieved by amino acid substitution, addition or deletion, wherein the alteration of the amino acid sequence results in a reduced capacity for the polypeptide to engage in the HLA-DM catalysed peptide exchange reaction;

use of HLA-DO analogues or derivatives to suppress HLA-DM catalysed exchange of peptides;

use of HLA-DM analogues or derivatives to suppress HLA-DM catalysed exchange of peptides;

an accordingly altered polypeptide, wherein the alteration is conducted within a sequence recognised as a T-cell epitope wherein said loss of immunogenicity is achieved by amino acid substitution, addition or deletion, wherein the alteration of the amino acid sequence is conducted at a position which in the non-modified polypeptide is a T-cell epitope and the alteration renders the T-cell epitope unable to survive the processing pathway for MHC class II presentation for reason of peptide cleavage;

a method in which knowledge of protease recognition sites in a protein of interest is used in making the decision which potential T-cell epitopes have to be removed from this protein;

a polypeptide containing a T-cell epitope in which one or more amino acid changes in the N-terminal and/or C-terminal flanking regions of said epitope are conducted such that one or more protease recognition sites are rendered resistant to these proteases;

a polypeptide containing a T-cell epitope in which one or more amino acid changes are conducted such that a novel protease site is introduced in the epitope a polypeptide in which one or more amino acid changes are conducted such as to create a B-cell asparaginyl endopeptidase cleavage site;

a polypeptide in which one or more amino acid changes are conducted such as to create a cathepsin site;

a polypeptide in which one or more surface exposed asparagine residues are substituted for an alternative amino acid;

a polypeptide in which one or more surface exposed asparagine residues are substituted for a glutamine residue;

a polypeptide in which all surface exposed asparagine residues are substituted for an alternative amino acid;

a method of reducing the immunogenic potential of a polypeptide involving a step whereby protease cleavage pattern of the polypeptide is analysed by any means;

a method of reducing the immunogenic potential of a polypeptide involving a step whereby protease cleavage pattern of the polypeptide is analysed using an in silico technique;

a method of reducing the immunogenic potential of a polypeptide involving the alteration of the protease cleavage pattern of the polypeptide;

a method of reducing the immunogenic potential of a polypeptide involving the alteration of the protease cleavage pattern of the polypeptide by introducing into the sequence of the polypeptide one or more additional cleavage site(s);

a method of reducing the immunogenic potential of a polypeptide involving the alteration of the protease cleavage pattern of the polypeptide by removing one or more cleavage sites in the polypeptide;

a modified polypeptide whereby the modification being of any of the types described above or below specifically acts to result in loss of binding capability with the MHC class II peptide binding groove once the polypeptide has been processed for presentation within the APC;

a method for reducing the immunogenicity of a therapeutic protein by introducing into the protein one or more copies of a peptide sequence capable of efficient presentation on MHC class II;

a method for reducing the immunogenicity of a therapeutic protein by introducing into the protein one or more copies of a peptide sequence capable of efficient presentation on MHC class II and where multiple copies are linked in serial array each peptide unit is flanked by a protease cleavage site;

an accordingly specified method wherein the appended peptide sequence is a self peptide an accordingly specified method wherein the appended peptide sequence is a self peptide sequence AILEFRAMAQFSRKTD (SEQ ID NO:1)

a modified polypeptide of structure [X]nY, where X=self peptide with pan reactive binding to multiple MHC allotypes, n=any whole number including 1, Y=therapeutic protein;

an accordingly specified polypeptide structure but where X=AILEFRAMAQFSRKTD (SEQ ID NO:1)

an accordingly specified polypeptide structure but where X contains a C-terminal proteinase cleavage site especially for any of the cathepsins of TABLE 1;

a modified polypeptide of structure Y-[X]n, where X=self peptide with pan reactive binding to multiple MHC allotypes, n=any whole number including 1, Y=therapeutic protein;

an accordingly specified polypeptide structure but where X contains a N-terminal proteinase cleavage site especially for any of the cathepsins of TABLE 1, a modified polypeptide of structure [X']n-Y-[X"]n, where X=self peptide with pan reactive binding to multiple MHC allotypes, n=any whole number including 1, Y=therapeutic protein;

an accordingly modified polypeptide structure but where X'=X"

an accordingly modified polypeptide structure but where X' contains C-terminal protease cleavage site and X" contains an N-terminal cleavage site;

a modified polypeptide of structure [X]nY, where X=self peptide with pan reactive binding to multiple MHC allotypes, n=any whole number including 1, Y=therapeutic protein;

The term "peptide" as used herein and in the appended claims, is a compound that includes two or more amino acids. The amino acids are linked together by a peptide bond (defined herein below). There are 20 different naturally occurring amino acids involved in the biological production of peptides, and any number of them may be linked in any order to form a peptide chain or ring. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Some peptides contain only a few amino acid units. Short peptides, e.g., having less than ten amino acid units, are sometimes referred to as "oligopeptides". Other peptides contain a large number of amino acid residues, e.g. up to 100 or more, and are referred to as "polypeptides". By convention, a "polypeptide" may be considered as any peptide chain containing three or more amino acids, whereas a "oligopeptide" is usually considered as a particular type of "short" polypeptide. Thus, as used herein, it is understood that any reference to a "polypeptide" also includes an oligopeptide. Further, any reference to a "peptide" includes polypeptides, oligopeptides, and proteins. Each different arrangement of amino acids forms different polypeptides or proteins. The number of polypeptides—and hence the number of different proteins—that can be formed is practically unlimited.

The MHC class I/peptide complex on the APC surface presents a binding face to a particular T cell receptor TCR) able to recognise determinants provided both by exposed residues of the peptide and the MHC class II molecule. Any peptide binding to a MHC class II molecule and engaging a TCR to promote an immune response is commonly defined as an epitope and in particular a functional T cell epitope.

DETAILED DESCRIPTION OF THE INVENTION

It is a particular objective of the present invention to provide modified polypeptides with reduced capacity for presentation to the immune system by the MHC class U pathway. In a first embodiment, the polypeptide is modified by amino acid substitution and the substitution concerned is for one or more specific amino acid residues within the polypeptide chain to be changed for their respective D-isomeric forms.

Inclusion of a single D-amino acid within a polypeptide is known to disrupt binding to the MHC class II binding groove. U.S. Pat. No. 5,679,640 shows that substitution for a D-amino acid is required to be made at a critical contact site for the peptide MHC complex and substitution to a D-amino acid at non critical sites is tolerated within the MHC/peptide complex. The intent of the present invention is to exploit substitution of a D-amino acid to disrupt binding within the MHC class II binding pocket such that the peptide fails to be presented to the TCR. This is distinct from the methods taught by U.S. Pat. No. 5,679,640 where substitution occurs at a non critical binding residue in a strategy seeking to displace an auto-antigenic peptide with a auto-antigen surrogate retaining a high affinity for the MHC but which fails to enable recognition and binding with the TCR.

In the art there are a number of examples where polypeptide therapeutics have been described and which feature one or more D-amino acid residues within the primary structure. These would include U.S. Pat. No. 5,182,261; U.S. Pat. No. 5,668,109; U.S. Pat. No. 4,764,504; U.S. Pat. No. 5,948,764; U.S. Pat. No. 5,545,618; U.S. Pat. No. 5,877,156; U.S. Pat. No. 5,932,545; U.S. Pat. No. 6,087,441 and others where wholly synthetic peptide entities containing one or more D-amino acid residues have been produced. Usually such substitutions are in combination with additional modifications to the N and or C terminal residues with the intention of conferring stability in vivo through a reduced propensity to undergo peptidase degradation. D-amino acids themselves show a reduced propensity to enzymatic attack thereby contributing to in vivo stability but in the contexts of the above cited examples, the D-amino acids have been included at particular positions to confer antagonistic activities to their constituent synthetic peptides usually by providing enhanced binding to a biological target and blockade of some biological activity for potential or actual therapeutic benefit.

Thus U.S. Pat. No. 5,985,242 discloses synthetic beta-amyloid peptide analogues featuring D-amino acids which are proposed to bind the naturally occurring beta-amyloid peptide component of the nascent neurofibrilary tangles present in amyloidogenic diseases such as Alzheimers disease. By so binding, the peptide analogues inhibit further aggregation. Similarly, peptide analogues of human myelin basic protein (MBP) containing D-amino acids have been described. In one embodiment of U.S. Pat. No. 5,948,764 peptides of at least 7 amino acids and preferably encompassing residues 86-99 of the human MBP are described. Peptides including residue 87 which would otherwise be an L-valine are modified to include a D-amino acid at this position such that the peptide analogue achieves increased binding to MHC relative to the native MBP 87-99. A typical modification will include L-valine to D-valine or another D-amino acid.

It is a common practice in the art and especially in the field of synthetic peptide therapeutics to include "capping" structures at the N and or C terminus of the peptide and serve to increase the in vivo half-life of the peptide. Thus from the examples above, in U.S. Pat. No. 5,985,242 terminal modifications in addition to the inclusion of D-amino acids within the sequence tract include C-terminal amidation, alkylation or addition of aryl amide or hydroxyl groups. Modifications to the N-terminus are also disclosed and include addition of cyclic, heterocyclic, polycyclic and or branched alkyl groups and in the art numerous other chemical groups or linkages have been contemplated with the purpose of rendering the polypeptide termini stable within the in vivo milieu.

Exploitation of a non-natural enatiomeric form of amino acids such as a D-amino acid is a strategy available for therapeutics produced by chemical synthesis. Incorporation of D-amino acids into polypeptide therapeutics with large molecular mass as produced using recombinant expression systems is not achievable. Whilst a number of microbial derived fermentation systems and purified enzymes from bacterial, fungal and other biological sources are able to interconvert racemic forms of free amino-acids, the enzymology to enable racemisation of an amino-acid residue within a polypeptide chain to the inventors knowledge is not known in the art. The discovery of such enzymatic capability would have obvious utility under the scheme of the present invention.

A second embodiment of the invention encompasses covalent attachment of a chemical group to the polypeptide therapeutic protein. The appended attachment will hinder one or more of the antigen processing steps outlined herein above and will culminate in a reduced propensity for the segment of polypeptide sequence to which the attachment is coupled to become represented in the MHC/peptide repertoire on the surface of an APC. It is most preferred that the incoming chemical group is attached to the polypeptide chain at a single desired site. Alternative configurations are also contemplated whereby modification by covalent attachment occurs at a number of desired sites and or at sites specified by particular primary structural contexts of the polypeptide.

In the art methods exist for the modification of polypeptides by covalent attachment of large chemical groups or appendages such as glycan derivatives, polyethylene glycol derivatives lipid moieties and the like [for examples see U.S. Pat. No. 5,885,570; WO0026230; WO90/13590 and others]. Other modifications such as attachment of a single carbon acetyl group have also been disclosed [WO0035427], and have been conducted with the intent of enhancing the bioavailability of the therapeutic by steric blockade of particular receptor sites on the molecule and or via a generalised mechanism of immune surveillance escape.

A particular example of one such envisaged chemical modification which for the purpose of the invention is considered especially suited, is the addition of an Asn-linked glycosylation to the polypeptide chain. The consensus signal sequence for providing an Asn-linked glycosylation is well defined as Asn-X-Ser/Thr where X is any amino acid except Pro (three letter codes). It is of course recognised that the generation of an Asn-X-Ser/Thr motif by single amino acid substitution within any defined epitope will be an unlikely practical possibility for most epitopes as their core sequence will be far different from this motif. In this regard multiple substitution of amino acids to give rise to this signal sequence are proposed and fall within the scope of the present invention.

Other glycosylation linkages are understood in the art such as O-linked glycosylation which involves either simple oligosaccharide chains or glycosamino glycan chains [Alberts. B. et al (1990) *Molecular Biology of the Cell* 2$^{nd}$ edition, Garland Publishing Inc. New York pp 433-475] and fall within the scope of the invention.

It is recognised that glycosylated peptides (e.g. Asn-linked glycan) are stable and are not able to be exported from the cytosol to the ER lumen by TAP [Momburg F. M. et al (1994) *J. Exp. Med.* 179: 533] a critical component of MHC class I processing pathway. Moreover most naturally processed peptides do not contain an N-linked glycan consensus sequence, there is reasonable expectation that processing and trafficking of glycan peptides within the MHC class II pathway will be influenced by the presence of the glycose determinant and further augment the inability for the peptide to associate with the MHC class II binding groove.

It is understood therefore that glycosylation of a polypeptide may result in a species less immunogenic than a non-glycosylated species of otherwise identical structure. A further embodiment of the present invention is to provide a polypeptide species in which a glycosylation signal or a site of glycosylation is removed such that the resultant polypeptide species is more immunogenic than its non-glycosylated counterpart. This situation may be desired for example in the case of vaccine molecules whereby the intent is to focus an immune response to a particular molecular species.

It is preferred that covalent modification of a polypeptide using the present invention occurs at a minimum number of sites. It is particularly preferred that covalent modifications are directed to defined residues within the primary structure of the polypeptide. Methods for directing chemical attachments to particular residues or classes of amino acid residue within a polypeptide molecule are well known and may be exploited under the scope of the present invention to achieve modification according to the preferred embodiments. Thus chemical modification schemes to enable targeted linkage to available amide groups on Lys residues, or to carboxylic groups carried on Asp or Glu residues or activation of sulphydryls on Cys residues are well documented [see for example *Bioconjugate Techniques*, (1996) Hermanson G. T. Acedemic Press Inc; Aslam M. & Dent A. *Bioconjugation* (1998) Macmillan, London] and may be exploited under the scheme of the present invention. Similarly, methods for the activation and coupling of polymeric molecules such as PEG are intensively described in the art [for example schemes see U.S. Pat. No. 5,349,001 and WO90/13590] and analogous schemes for coupling other moieties of lipid or amide or glycose or other chemical character can be identified in the art as suitable for exploitation under the scheme of the present invention.

Where the present invention relates to methods for the reduction in immunogenic potential of a therapeutic protein, a fourth general modality by which this is achieved includes an embodiment whereby the therapeutic polypeptide is modified at one or more specific regions within its sequence of amino acid residues. The modification may be substitution, deletion or addition of an amino acid residue and the result of such a modification is to alter the recognition of the polypeptide by one or more of the critical proteases involved in peptide degradation whereby a processed peptide epitope ultimately may become associated with an MHC class II binding groove.

It is a specific embodiment of this invention to mutate or modify residues that are flanking peptides with the proven or predicted potential to bind to the MHC class II molecules HLA-DR, DQ and DP, such that these peptides can no longer be excised from the antigenic protein by the proteases involved in protein processing in the MHC class II pathway.

A further embodiment is the modification of protein sequences that have the proven or predicted potential to bind to HLA-DR, DQ and DP molecules, such that these sequences will become susceptible to proteases involved in the NHC class II processing pathway. This also is achieved by making amino acid changes such that motifs are created that can be recognised and cut by proteases involved in the MHC class II pathway.

In a yet further embodiment the information about proteolytic processing sites in a protein of interest is of itself valuable data that can be used in a predictive manner to identify peptides with the potential to bind to HLA-DR, DQ or DP and are therefore likely to be found on the surface of the APC.

The protease asparagine endopeptidase plays a crucial role in the processing of antigens taken up by B-cells. The enzyme was shown to play a crucial role in the degradation of a tetanus toxin domain in disrupted lysosomes from human B-cells [Manouri et al., (2000) *Nature* 396: 695-699]. The cleavage sites of the B-cell asparaginyl endopeptidase are dependent on both the sequence and the structure of the target protein. There is an appreciation that the polypeptide antigen is first digested with this protease, to result in the disclosure of sites sensitive to other proteases like cathepsins, which are necessary for further processing. The processing of the tetanus toxin C fragment by the asparaginyl endopeptidase could be inhibited by N-glycosylation of Asn-residues of the antigen. The enzyme also plays a role in protein processing in thymic APCs [Mannoury et al., (2002) *Nat. Immunol* 3:169-174; Anderton et al., (2002) *Nat. Immunol.* 3:175-181], where it has been shown to remove a cryptic epitope of myelin basic protein, containing a central apsarigine.

Accordingly, a polypeptide under the scheme of the present may be rendered less immunogenic by the removal of surface exposed asparagines residues. Removal is achieved by amino acid substitution and most conveniently using the techniques of recombiant DNA manipulation although other schemes may be contemplated for example chemical deamidation or chemical synthesis. In the first instance a particularly good substitution would be to replace asparagines with gluatamine although other replacements such as aspartic acid or glutamic acid may equally be considered.

Another protease, which was solely found in the thymus, is thymus-specific serine protease. The gene encoding this protein is located in the MHC class I region. Expression of this protein was not observed in other APCs. The exclusive expression of this enzyme and the specific role of cathepsin L in thymic cells (see above) indicate that the proteolytic environment in thymic cells is rather unique.

Because several of the above-mentioned proteases are involved in other physiological processes as well, the mechanism and specificities of some these proteases have been analysed. TABLE 1 summarises the specificities for a number of significant cathepsins.

TABLE 1

| Cathepsin | Key Properties |
| --- | --- |
| Cathepsin L | Cysteine endopeptidase. Hydrolysis of proteins with broad specificity for peptide bonds, with preference for a residue bearing a large hydrophobic side chain at the P2 position (P2: i.e. 2nd. amino acid in N- |

TABLE 1-continued

| Cathepsin | Key Properties |
|---|---|
| | terminal direction relative to point of cleavage). Does not accept Val at P1'. Preferential cleavage of Gly—Gly bond in peptides. As compared to cathepsin B, cathepsin L exhibits higher activity towards protein substrates, but has little activity on Z—Arg—Arg—NHMec, and no peptidyl-dipeptidase activity. |
| Cathepsin S | Similar to cathepsin L, but with much less activity on Z—Phe—Arg—\|—NHMec, and more activity on the Z—Val—Val—Arg—\|—Xaa compound. |
| Cathepsin D | P1 site: hydrolytic residues that are branched at the beta-carbon are preferred, except Ile and Val; P1'site: strong hydrophobicities; P2 site: weak hydrophobicities. |
| Cathepsin E | Similar to cathepsin D, but slightly broader specificity. |
| Cathepsin B | Hydrolysis of proteins with broad specificity for peptide bonds. Preferentially cleaves —Arg—Arg—\|—Xaa bonds in small molecule substrates (thus differing from cathepsin L). In addition to being an endopeptidase, shows peptidyl-dipeptidase activity, liberating C-terminal dipeptides. Preference for aromatic residues e.g. Phe in P2 position. |
| Cathepsin K | Broad proteolytic activity. With small-molecule substrates and inhibitors, the major determinant of specificity is P2, which is preferably Leu, Met > Phe, and not Arg. |
| Cathepsin H | Hydrolysis of proteins, acting as an aminopeptidase (notably, cleaving Arg—\|—Xaa bonds) as well as an endopeptidase. |

Where it is an object of the current invention to modify antigenic proteins such that sites processed by proteases involved in the proteolytic pathway of MHC class II presentation will be made insensitive to these proteases, leading to a reduction in the presentation of antigenic peptides on the surface of antigen presenting cells; another object is to introduce additional protease sites in T-cell epitopes of antigenic proteins such that these epitopes will be further processed in the endocytic vesicles and no longer can be presented to the immune system. Such mutations are distinct from those directed to the removal or disruption of the epitope per se, but rather results in a decreased likelihood for a potential MHC class II ligand to emerge from the processing pathway and become presented on the surface of the APC. Thus under the scheme of the present, it is not an objective necessarily to mutate MHC anchor residues of the antigenic peptides although mutations of the present may be conducted in combination with such a strategy.

A number of approaches have been adopted to identifying the nature of the peptides presented on the surface of APC via the MHC class II systems herein outlined. By way of example, it has been possible to purify antigenic peptides from the surface of antigen charged APCs and apply protein sequencing techniques to the extracted peptides. Alternatively libraries of synthetic (overlapping) peptides, that constitute a certain protein of interest, have been bound to antigen presenting cells or purified HLA-DR, DQ or DP molecules, followed by elution and sequence analysis of those peptides that interact with these proteins. A further approach has been to predict which peptides of a certain protein of interest are likely to bind to HLA-DR molecules, on the basis of consensus binding motifs or by X-ray diffraction/structure modelling of HLA-DR molecules or other in silico based techniques such as peptide docking.

In principle all of these approaches are able to yield information about the sequence of peptides with the potential to bind to MHC molecules and such data can be used to make mutations in peptides or in the proteins from which the peptides were derived, such that the interactions with MHC molecules are severely hampered. The mutations that can be made in proteins to achieve this are usually restricted to those residues of antigenic peptides that tightly bind in the peptide-binding groove of HLA-DR, DQ or DP, the so-called anchor residues. Although these mutations for most epitopes are sufficient to reduce antigenicity, some epitopes are more difficult to remove since mutations at these positions seriously affect the functional activity of the protein. The present invention is conceived to overcome this limitation.

When use is made of peptide libraries for the selection of DR binding peptides, peptides may be found that have the potential to bind to DR molecules, but that will never occur in antigen presenting cells because the proteolytic pathways in these cells do not allow this peptide to emerge from the antigenic protein. The same can be said about peptides that are predicted to bind to DR or DQ molecules by computer algorithms. As a consequence, both methods can lead to an overprediction of the number of peptides that may play a role in the immune response against a protein. The ability to determine which of these predicted potential T-cell epitopes are likely to be presented on antigen presenting cells requires additional information about protease sites in the protein.

According to the present invention a preferred method for the removal of protease processing sites is as follows:
1. For a given protein of interest (part of) the sequence is determined.
2. Peptides that have the potential to bind to HLA-DR, HLA-DQ or HLA DP molecules are identified.
3. Stretches of amino acids flanking these epitopes are analysed for the presence of motifs that may be recognized by proteases involved in the MHC class II processing pathway, especially proteases detailed in TABLE 1.
4. Mutations are designed such that proteases can no longer recognise and cut at these positions.
5. Mutations are introduced in the protein of interest by any of the now standard molecular biological techniques.
6. Optionally, modified molecules are re-analysed to verify loss of protease sensitivity at the desired region(s) and reduced ability of the peptide to be presented at the cell surface in association with MHC class II.

In the practice of the above method, step 3 may optionally be conducted exploiting proteolytic protein extracts from antigen presenting cells. The protein of interest is incubated with the extract and it this can be done under a range of conditions (e.g. multiple pH points). Digestion products of the protein of interest may be analysed for example using HPLC purification of various fragments, followed by identification of their sequence using Edman degradation and/or mass spectrometry. According to this scheme, alignment of the sequence of the fragments found with the sequence of the protein of interest indicates the positions at which proteases have cut to enable design of rational mutations such that proteases can no longer recognise and cut at these positions.

According to the present invention a preferred method for the reduction of immunogenicity by the introduction of additional processing sites is as follows:
1. For a given protein of interest (part of) the sequence is determined.
2. Peptides that have the potential to bind to HLA-DR, HLA-DQ or HLA DP molecules are identified.
3. In the peptides that are identified as T-cell epitopes mutations are designed that introduce protease recognition motifs, such that digestion with that protease can take place between the first and the last anchor residue of that T-cell epitope
4. Mutations are introduced in the protein of interest by any of the now standard molecular biological techniques.

5. Optionally, modified molecules are re-analysed to verify loss of protease sensitivity at the desired region(s) and reduced ability of the peptide to be presented at the cell surface in association with MHC class II.

The practice of the above method may be particularly preferred in a situation where multiple overlapping T-cell epitopes are detected. The requirement according to step 3 of the above method whereby a de novo processing site is introduced between the first and last anchor residue of a defined epitope may not be practicable to define unless a fine detail epitope map has been drawn up to the point whereby the critical nonamer peptides are identified. In all practicality, it is recognised that where a multitude of MHC class II allotypes (especially HLA DR) are to be considered, the nonomer sequence for one allotype may "slip" in register with the nonomer sequence for a similar allotypic specificity binding the same epitope, and a series of overlapping nonomers can be defined within a sequence exceeding 9 residues in length. In such a situation the de novo cleavage site so defined in step 3 may fall outside the region between the first and last anchor residue for the epitope and yet cleavage will still result in a loss of peptide presentation via MHC class II. Such mutational change will be considered to fall under the scope of the present.

In a yet further embodiment the information about proteolytic processing sites in a protein of interest is of itself valuable data that can be used in a predictive manner to identify peptides with the potential to bind to HLA-DR, DQ or DP. As described above, T-cell epitope prediction algorithms and the selection of peptides from libraries of overlapping peptides for their ability to bind to HLA-DR, DQ or DP molecules, will almost inevitably lead to an overprediction of the number of T-cell epitopes. When potential T-cell epitopes are predicted that contain a recognition motif for cleavage by a protease involved in the MHC class II processing pathway, the chance that this epitope will be found in nature is reduced and hence removing this epitope from the protein of interest is not essential. Also, when potential T-cell epitopes are predicted that are not flanked by protease recognition sites, the chance that such an epitope is excised from the protein and is presented on the surface of the antigen presenting cell is reduced and hence removing this epitope from the protein of interest is not essential.

According to this further embodiment of the present invention a preferred method for targeting critical T-cell epitopes for removal is as follows:
1. For a given protein of interest the sequence is determined.
2. Potential T-cell epitopes are predicted in the sequence
3. All Potential T-cell epitopes are scrutinised for the presence of motifs within the binding region, that are likely to be recognised by proteases involved in the MHC class II proteolytic pathway.
4. All Potential T-cell epitopes found to contain a protease cleavage site within 10 amino acids C-terminally or N-terminally of the potential T-cell epitope are considered critical for epitope removal. All Potential epitopes that lack these motifs are considered less critical and may be excluded from the set of epitopes requiring removal from the protein of interest.

Where the present invention relates to methods for the reduction in immunogenic potential of a therapeutic protein, a fourth general modality by which this is achieved includes an embodiment whereby the therapeutic polypeptide is modified at one or more specific regions within its sequence of amino acid residues. The modification may be substitution, deletion or addition of an amino acid residue and the result of such a modification is to alter the efficiency in which the critical HLA-DM catalysed reaction where a processed peptide epitope becomes associated with an MHC class II binding groove.

Although the main determinant for peptide exchange of an epitope by HLA-DM is the affinity of the peptide for HLA-DR, there is increasing evidence that amino acid residues that do not determine the binding affinity for HLA-DR can also have an effect on the exchange reaction. It has been shown that the presence of HLA-DM in in vitro peptide exchange reactions using synthetic peptides with HLA-DR-CLIP can have a large influence on the choice of peptides that will replace the CLIP peptide. Lightstone et al. [Lightstone et al (1997); *Proc. Natl. Acad. Sci. USA* 94: 9255-9260] compared the expression of self-peptide on the surface of normal, Ii⁻, HLA-DM⁻ and LA-DM/Ii⁻ antigen presenting cells, and noticed a profound difference in the array of peptides that were presented on cells with or without HLA-DM expression. Kropshofer et al. [Kropshofer et al (1996); *EMBO J.* 15:6144-6154] used an affinity purification method to obtain HLA-DR molecules (DR2 and DR3 allotypes) from EBV-transformed lymphoblastoid cells and incubated these for 16 hrs at pH 5 in the presence or absence of HLA-DM. The peptides that remained complexed were eluted off and analysed by mass spectrometry. When the spectra were compared it was clear that some peptides were efficiently removed by HLA-DM, whereas others were not affected. In another experiment, when a mixture of six different self-peptides, previously eluted from HLA-DR1 was tested in a binding assay, five of them bound efficiently to DR1 in the absence of DM and in the presence of DM, only two of these remained associated. These and other experiments have led to the idea that HLA-DM has the potential to function as a peptide editor that selects a certain subpopulation of peptides for presentation at the cell surface. It has become evident that some other factor than the affinity of these peptides for HLA-DR plays a role: the kinetic stability of the complex. Although stability and affinity are related ($K_D=k_{off}/k_{on}$), the $k_{off}$ has a profound effect on the efficiency of the HLA-DM catalysed exchange reaction. This is exemplified by the CLIP peptide, which has an exceptionally high $k_{on}$ and also a high $k_{off}$. As a consequence, the affinity is relatively high, but the stability (in the presence of DM) is low. The role of HLA-DM can thus be described as kinetic proofreading.

Several attempts have been made to analyse which amino acids at certain positions of a potential T-cell epitope will influence the efficiency of the HLA-DM catalysed exchange reaction. Kropshofer et al. [Kropshofer et al (1996); *EMBO J.* 15:6144-6154] analysed the effect of mutations at anchor positions of the HA(307-319) peptide on in vitro binding to HLA-DR1. A tyrosine at anchor residue 1 fits very well in the first pocket of the binding groove. Replacing this by an aspartic acid abolishes binding. A methionine or valine at this position can still give good binding, but in the presence of HLA binding is reduced. Hence (sub)optimal residues at anchor positions can be selected against by HLA-DM. A similar observation was made for pocket residue 9. In pocket 6 a moderate opposite effect was observed: HLA-DM allowed the binding of residues that were disfavoured in its absence. HLA-DM also selects against epitopes shorter then 11 amino acids, reflecting the size of DR-bound peptides found in nature.

Raddrizzani et al. [Raddrizzani et al (1999); *Eur. J. Immunol.* 29, 660-668] showed that (synthetic) peptides that are most likely to be released from HLA-DR by HLA-DM in vitro which are rich in glycine and proline residues. A possible explanation may be the fact that glycines and prolines can have a relatively large effect on the secondary structure of a peptide. Indeed when peptides with a high affinity for HLA-DR1 were compared with variant peptides in which glycines or prolines either were introduced or removed, a significant effect on the HLA-DM catalysed exchange reaction in vitro was observed.

The foregoing is to be taken as introduction to a yet further important embodiment of the present invention wherein there is a method concerned with modifying polypeptides such that one or more species of processed peptides from the polypeptide antigen are hindered or at least show reduced ability to participate in an HLA-DM catalysed peptide exchange reaction. This is achieved by mutating a protein of interest in such a way that certain peptides that have the ability to bind to HLA-DR, DQ and DP will become unfavourable in this exchange reaction.

A general method under this embodiment of the invention is as follows:
1. For a given protein of interest (part of) the sequence is determined.
2. Peptides that have the potential to bind to HLA-DR, HLA-DQ or HLA-DP molecules are identified.
3. Mutations are designed in these (potential) T-cell epitopes that will reduce the efficiency of the HLA-DM catalysed exchange reaction with the HLA-DR-CLIP complex.
4. Mutations are introduced in the protein of interest by any of the now standard molecular biological techniques.

Mutations that are designed to reduce the efficiency of the HLA-DR catalysed exchange reaction with CLIP peptide bound to HLA-DR complexes may be made at any position in the (potential) T-cell epitopes. This includes positions that are likely to bind in the pockets of the antigen-binding groove of HLA-DR. Some mutations at these positions may not influence the affinity of the peptide for HLA-DR, but may reduce the efficiency of the HLA-DR catalysed exchange reaction. Furthermore such mutations may be made at non-anchor positions.

In a yet further embodiment of the present invention, and, as an alternative to manipulation of peptide sequences to influence HLA-DM catalysed exchange, such exchange could be altered via manipulation or mimickry of HLA-DM or HLA-DO molecules themselves. For example, HLA-DO molecules or other molecules which mimic the action of HLA-DO could be introduced into APCs other than B cells (where they are present) either by endocytosis of exogenously supplied HLA-DO (or its mimics) or by introduction of genes encoding HLA-DO or by activation of resident HLA-DO genes. Such HLA-DO molecules might, in practice, be subject to modifications (such as by amino acid changes) which alter the pH-dependant behaviour of HLA-DO such that, for example, the molecule might inhibit HLA-DM activity at pH5 or lower thus blocking HLA-DM catalysed exchange of peptides. Similarly, HLA-DM molecules or other molecules which mimic the action of HLA-DM could be introduced into APCs in order to improve the efficiency of peptide exchange or, with appropriate modifications to HLA-DM, to resist the inhibitory action of HLA-DO or to change the specificity for peptides bound by HLA-DM or to change the pH sensitivity of HLA-DM. Thus, manipulation or mimickry of HLA-DO or HLA-DM could either enhance the presentation of specific peptides on HLA-DP, DQ or DR or reduce/eliminate such presentation.

In a yet further still embodiment of the invention, specific protease recognition sites can be included adjacent to or within a specific HLA binding peptide such that the protease site is differentially susceptible to cleavage in different APC's. By this method, peptides may be preferentially released from within a protein sequence by specific APC's in order to influence the type T cells response resultant from subsequent presentation of peptides on the APC's. For example, preferential release of peptides from dendritic cells (e.g. by preferential inclusion of flanking cathepsin S sites) might then induce a different type cellular response (e.g. TH1 biased) compared to that induced by processing of the same protein in macrophages. Thus, the balance of TH0, TH1 and TH2 responses induced by the same protein might be influenced by judicious inclusion of flanking or internal protease sites. Similarly, the differential pattern of proteases within different APC's might be utilised to influence the trafficking of peptides within the APC's. A particularly favourable scheme to disturb the dynamics of peptide presentation at the surface of the APC is to provide in with the therapeutic polypeptide antigen, peptide sequences which by virtue of their sequence and abundance, are able to preferentially gain presentation to the outside surface via the MHC system. In so doing these preferentially presented peptides will out-compete those other peptides present in the antigenic protein and so those peptides will not be available for initiating an immune response. Critical to the usefulness of such an approach of course is that the preferentially presented peptides themselves are incapable of evoking an immune response. Implicit in the design of such a scheme therefore is the use of a self peptide antigen, i.e. a peptide from the host organism to which the organism has established high level immunological tolerance.

In addition to the need for a self tolerant sequence, a peptide with efficacy in such a scheme that may be termed "immune quenching" should also have the property of high affinity for broad range of MHC and preferably HLA-DR allotypes, also high kinetic stability in the presence of HLA-DM. A peptide that has the above-mentioned characteristics is termed Self-peptide SP3 with the sequence in single letter code: AILEFRAMAQFSRKTD (SEQ ID NO:1).

Under the scheme of the present invention, SP3 or a functionally equivalent peptide sequence is linked to either the C-terminus and or the N-terminus of a therapeutic protein of interest. The peptide is preferably flanked on either side by a recognition motif for a protease involved in the MHC class II processing pathway such as any or more depicted in TABLE 1. The peptide may be linked in tandem repeat to the N and or C-terminus of the therapeutic protein. The means to engineer such a construct are readily available in the art and structures featuring any number of repeating units could be envisaged and fall under the scope of the present.

The invention claimed is:

1. A method for the production of an immunogenically modified protein or polypeptide having a specific biological activity and being substantially non-immunogenic or less immunogenic than any non-modified target protein or polypeptide having the same biological activity when used in vivo, the method comprising the following steps:
   (i) determining the amino acid sequence of at least a portion of a target protein or polypeptide;
   (ii) identifying at least one potential T-cell epitope on said sequence having the potential to bind the HLA-DR allotypes to which the polypeptide of SEQ ID NO: 1 binds using standard methods;
   (iii) modifying the target protein or polypeptide by introducing at the C-terminus or N-terminus of the target protein or polypeptide one or more copies of a peptide of sequence AILEFRAMAQFSRKTD (SEQ ID NO: 1), wherein the peptide of sequence AILEFRAMAQFS-RKTD (SEQ ID NO: 1) is attached to the C-terminus or N-terminus by a protease cleavage site involved in the MHC class II processing pathway.

2. The method of claim 1, wherein multiple copies of the peptide of SEQ ID NO: 1 are linked in serial array, each copy being flanked by a protease cleavage site.

3. The method of claim 2, wherein the protease cleavage site is specific for a protease selected from the group consisting of Cathepsin L, Cathepsin S, Cathepsin D, Cathepsin E, Cathepsin B, Cathepsin K and Cathepsin H.

* * * * *